United States Patent [19]

Shaw et al.

[11] 4,115,441
[45] Sep. 19, 1978

[54] CATALYST COMPOSITIONS ESPECIALLY USEFUL FOR PREPARATION OF UNSATURATED ACIDS

[75] Inventors: Wilfrid G. Shaw, Lyndhurst; David B. Terrill, Bedford, both of Ohio

[73] Assignee: The Standard Oil Company, Cleveland, Ohio

[21] Appl. No.: 755,708

[22] Filed: Dec. 30, 1976

Related U.S. Application Data

[62] Division of Ser. No. 686,352, May 14, 1976.

[51] Int. Cl.$^2$ .............................................. C07C 57/04
[52] U.S. Cl. .................................... 562/534; 562/535
[58] Field of Search ............... 252/435, 437, 462, 464, 252/465, 468, 469, 470; 260/530 N

[56] References Cited

U.S. PATENT DOCUMENTS

| | | | |
|---|---|---|---|
| 3,595,911 | 7/1971 | Ball | 260/530 N |
| 3,736,354 | 5/1973 | Yanagita et al. | 252/470 X |
| 3,875,220 | 4/1975 | White et al. | 252/464 X |
| 3,882,047 | 5/1975 | Niina et al. | 252/435 |
| 3,956,181 | 5/1976 | Grasselli et al. | 252/455 R X |
| 3,965,163 | 6/1976 | Oda et al. | 252/437 X |

FOREIGN PATENT DOCUMENTS 1,170,851  11/1969  United Kingdom.

*Primary Examiner*—Delbert E. Gantz
*Assistant Examiner*—William G. Wright
*Attorney, Agent, or Firm*—Evelyn R. Kosman; Herbert D. Knudsen; Larry W. Evans

[57] ABSTRACT

The present invention relates to a catalyst composition consisting of oxide complexes of vanadium, molybdenum and germanium plus an additional oxide selected from the group consisting of iron, nickel, thallium, phosphorus, indium, bismuth and the rare earths and optionally an oxide selected from the group copper, magnesium, manganese, aluminum, titanium, potassium, rubidium, cesium, niobium, tantalum, chromium, tungsten, uranium, cobalt, silver, zinc, tin, gallium, arsenic and antimony. These catalysts are especially useful for producing acrylic acid from acrolein and for producing methacrylic acid from methacrolein.

8 Claims, No Drawings

CATALYST COMPOSITIONS ESPECIALLY USEFUL FOR PREPARATION OF UNSATURATED ACIDS

This application is a divisional of application Ser. No. 686,352, filed May 14, 1976.

BACKGROUND OF THE INVENTION

Catalyst compositions similar to those of the present invention are disclosed in U.S. Pat. No. 3,736,354 which pertains to catalyst compositions containing the oxides of vanadium and molybdenum and one or more of the oxides of germanium, uranium, manganese, copper, gold and barium for the production of acrylic and methacrylic acids from acrolein or methacrolein. British Pat. No. 1,170,851 discloses catalyst compositions of the mixed oxides of molybdenum, vanadium and aluminum and an additional oxide such as germanium oxide, among others, for the production of acrylic acid from acrolein. However, the catalyst compositions of the present invention have heretofore not been disclosed wherein unexpectedly high yields of unsaturated carboxylic acids are obtained from the corresponding unsaturated aldehydes in the presence of these catalysts.

SUMMARY OF THE INVENTION

The present invention is a catalyst composition consisting of oxides or oxide complexes that contain catalytically significant amounts of vanadium, molybdenum and germanium, plus an additional oxide, wherein the additional oxide may be iron, nickel, thallium, phosphorus, indium, bismuth and the rare earths, and optionally an oxide selected from the group copper, magnesium, manganese, aluminum, titanium, potassium, rubidium, cesium, niobium, tantalum, chromium, tungsten, uranium, cobalt, silver, zinc, tin, gallium, arsenic and antimony. These catalysts are especially effective for preparing acrylic acid from acrolein and the preparation of methacrylic acid from methacrolein. The catalysts are also highly effective for oxidation reactions such as the oxidation of butadiene to maleic anhydride and the oxidation of the butenes and the aromatics to various oxygenated compounds. The catalysts of the present invention are highly reactive and are capable of very selectively oxidizing acrolein to acrylic acid with little acetic acid being formed.

The method of preparing these catalysts is not deemed critical. Normally, the catalysts of the invention are prepared by mixing the catalyst ingredients in the proper proportions in an aqueous mixture, drying the resulting aqueous slurry with or without a reducing agent, and calcining the product. The ingredients employed in the preparation of the catalysts can be the oxides, halides, nitrates, acetates or other salts of the particular compound added, and particularly preferred is the use of water soluble salts of the metal components. If a support is used, the material comprising the support may be incorporated into the catalyst along with the other ingredients, or the catalytic ingredient may be coated on an inert core. After the catalyst ingredients have been combined to form an aqueous slurry, the slurry is taken to dryness, and the dried solid obtained is heated in the presence of air at temperatures between about 200° to 600° C. This calcination can take place outside of the catalytic reactor or an in situ activation can be utilized.

More specifically, the catalysts of the invention are described by the following empirical formula:

$$Mo_aV_bGe_cX_dY_eO_f$$

wherein X is a member selected from the group consisting of iron, nickel, thallium, phosphorus, indium, bismuth and the rare earths; and Y is a member selected from the group copper, magnesium, manganese, aluminum, titanium, potassium, rubidium, cesium, niobium, tantalum, chromium, tungsten, uranium, cobalt, silver, zinc, tin, gallium, arsenic and antimony; and wherein $a$ is 6 to about 18;
$b$ is 0.1 to about 10;
$c$ is 0.1 to about 6;
$d$ is 0.01 to about 5;
$e$ is 0 to about 5; and
$f$ is the number of oxygens required to satisfy the valence requirements of the other elements present.

Preferred are catalysts wherein $a$ is a number from 9 to 15; $b$ is a number from 0.5 to 5; $c$ is a number from 0.5 to 3; $d$ is a number from 0.05 to 1; and $e$ is a number from 0 to 1.

The elements in those catalysts are present in the form of their oxides or oxide complexes. In addition to the active catalytic ingredients, the catalysts of the invention may contain material. Suitable support materials include silica, alumina, zirconia, titania, silicon carbide, boron phosphate and the like. Preferred support materials are silica, alumina or alundum.

As noted above, the catalysts of the invention are useful in a number of different oxidation reactions. Preferred among these reactions is the production of unsaturated acids from the corresponding unsaturated aldehydes. In such a process, acrylic acid or methacrylic acid is produced by reacting acrolein or methacrolein with molecular oxygen in the presence of steam at a temperature of about 200° to about 500° C. Of special interest is the preparation of acrylic acid from acrolein because of the extremely desirable results obtained.

The oxidation of unsaturated aldehydes to obtain the corresponding acid is well known in the art. Basically, the invention with respect to the process is the use of the new catalyst within the parameters of the known art process.

The known process involves the contacting of the unsaturated aldehyde with molecular oxygen in the presence of steam at a temperature of about 200° to about 500° C. The ratio of the reactants may vary widely, with molar ratios of molecular oxygen to the aldehyde of about 0.5 to about 5 normally being employed. Molecular oxygen is most conveniently added as air. The amount of steam may vary widely from the small amount generated in the reaction to 20 or more moles of steam per mole of aldehyde. In the preferred practice of the invention, about 1 to about 10 moles of steam per mole of aldehyde are added to the reactant feed.

The reaction may be conducted in a fixed or fluid-bed reactor using atmospheric, superatmospheric or subatmospheric pressure. The apparent contact time may vary considerably with contact times of a fraction of a second to 20 seconds or more normally being employed.

SPECIFIC EMBODIMENTS

Comparative Example A and Examples 1 to 8

The catalysts of the present invention (Examples 1 to 8) were prepared and compared to the known catalyst composition of U.S. Pat. No. 3,736,354, (Example A), for the reaction of the oxidation of acrolein to acrylic acid.

The catalysts of the comparative example was prepared as follows:

Comparative Example A $Mo_{12}V_3Ge_1O_{45.5}$

To 250 cc of hot distilled water was added 6.67 g. of ammonium metavanadate. After this reagent had dissolved with heating and stirring, 40.27 g. of ammonium heptamolybdate and then 1.99 g. $GeO_2$ were added. The resultant mixture was evaporated to near dryness with continued heating and stirring, and the contents placed in a drying oven at 120° C for 16 hours. The dried material was crushed and ground to pass through a 50-mesh screen. A sufficient amount of powder was employed to coat 3/16 inch alundum spheres to achieve a 20 weight percent coating on the spheres. The coated spheres were then dried at 120° C for three hours and then heat treated for two hours at 370° C.

The preparation of the catalysts in the Examples 1 to 8 representative of the invention are given below.

EXAMPLE 1

$Mo_{12}V_3Ge_1Fe_{0.1}O_{45.7}$

The procedure of Comparative Example A was repeated using 4.90 g. of ammonium metavanadate, 29.54 g. of ammonium heptamolybdate, 1.46 g. of germanium oxide ($GeO_2$) followed by 0.564 g. of ferric nitrate nonahydrate, and the catalyst completed as described.

EXAMPLE 2

$Mo_{12}V_3Ge_1Ni_{0.5}O_{46.3}$

The procedure of Example A was repeated using 6.55 g. of ammonium metavanadate, 39.52 g. of ammonium heptamolybdate, 1.95 g. of germanium oxide, and 2.71 g. of nickel nitrate hexahydrate, and the catalysts completed as described.

EXAMPLE 3

$Mo_{12}V_3Ge_1Tl_{0.2}O_{45.8}$

The procedure of Example A was repeated using 4.89 g. of ammonium metavanadate, 29.56 g. of ammonium heptamolybdate, 1.46 g. of germanium oxide and 1.06 g. of thallium acetate, and the catalyst completed as described.

EXAMPLE 4

$Mo_{12}V_3Ge_1P_{0.1}O_{45.8}$

The procedure of Example A was repeated using 4.98 g. of ammonium metavanadate, 30.10 g. of ammonium heptamolybdate, 1.48 g. of germanium oxide and 0.163 g. of 85% $H_3PO_4$, and the catalyst completed as described.

EXAMPLE 5

$Mo_{12}V_3Ge_1In_{0.2}O_{45.8}$

The procedure of Example A was repeated using 4.94 g. of ammonium metavanadate, 29.81 g. of ammonium heptamolybdate, 1.47 g. of germanium oxide, and 0.821 g. of indium acetate, and the catalyst completed as described.

EXAMPLE 6

$Mo_{12}V_3Ge_1Bi_{0.2}O_{45.8}$

The procedure of Example A was repeated using 4.89 g. of ammonium metavanadate, 29.50 g. of ammonium heptamolybdate, 1.46 g. of germanium oxide, and 0.65 g. of bismuth oxide, and the catalyst completed as described.

EXAMPLE 7

$Mo_{12}V_3Ge_1R.E._{0.5}O_{46.3}$

The procedure of Example A was repeated using 4.70 g. of ammonium metavanadate, 28.36 g. of ammonium heptamolybdate, 1.40 g. of germanium oxide, and 2.58 g. of rare earth trichloride hexahydrate, and the catalyst completed as described. If the rare earth chloride were in the oxide form, it would analyze as 46.2% total rare earth oxide of which $CeO_2 = 48.0\%$, $La_2O_3 = 33.0\%$, $Nd_2O_3 = 13.0\%$, $Pr_6O_{11} = 4.5\%$ and other rare earth oxides = 1.5%.

EXAMPLE 8

$Mo_{12}V_3Ge_1Tl_{0.2}Cu_{0.1}O_{45.9}$

The procedure of Example A was repeated using 4.87 g. of ammonium metavanadate, 29,45 g. of ammonium heptamolybdate, 1.45 g. of germanium oxide, 1.06 g. of thallium acetate, and 0.277 g. of cupric acetate, and the catalyst completed as described.

The catalysts prepared above were placed in a fixed bed reactor constructed of a 1.0 cm. inside diameter stainless steel tube having a reaction zone of 20 cc capacity. The reactor was heated in a split block furnace. The reactor was fed with a mixture of acrolein/air/$N_2$/steam in the molar ratio of 1/8.5/2.5/6. The apparent contact time was 2 seconds. The temperature of the surrounding block is given in Table 1. The results given in Table 1 are defined as follows:

$$\text{Conversion, \%} = \frac{\text{Moles of acrolein reacted} \times 100}{\text{Moles of acrolein fed}}$$

$$\text{Single Pass Yield, \%} = \frac{\text{Moles of product recovered} \times 100}{\text{Moles of acrolein fed}}$$

$$\text{Selectivity, \%} = \frac{\text{Moles of acrylic acid recovered} \times 100}{\text{Moles of acrolein reacted}}$$

The experimental results reported in Table 1 demonstrate the improvement obtained in the conversion of acrolein to acrylic acid with the use of the catalyst compositions of the present invention as compared with a catalyst of the prior art, in Comparative Example A.

TABLE 1

| OXIDATION OF ACROLEIN TO ACRYLIC ACID | | | | | | |
|---|---|---|---|---|---|---|
| | | | | % Single Pass Yield | | |
| Example | Catalyst (1) | Temp. °C | % Conversion | Acrylic Acid | Acetic Acid | % Selectivity |
| Comp. A | $Mo_{12}V_3Ge_1O_{45.5}$ | 300 | 87.5 | 83.0 | 0.8 | 94.8 |

TABLE 1-continued

OXIDATION OF ACROLEIN TO ACRYLIC ACID

| Example | Catalyst (1) | Temp. °C | % Conversion | % Single Pass Yield Acrylic Acid | Acetic Acid | % Selectivity |
|---|---|---|---|---|---|---|
| | $Mo_{12}V_3Ge_1O_{45.5}$ | 321 | 97.5 | 91.2 | 1.4 | 93.5 |
| 1 | $Mo_{12}V_3Ge_1Fe_{0.1}O_{45.7}$ | 302 | 97.4 | 93.2 | 1.1 | 95.7 |
| 2 | $Mo_{12}V_3Ge_1Ni_{0.5}O_{46.3}$ | 301 | 86.4 | 82.9 | 0.8 | 95.9 |
| 3 | $Mo_{12}V_3Ge_1Tl_{0.2}O_{45.8}$ | 309 | 98.8 | 93.0 | 1.4 | 94.1 |
| 4 | $Mo_{12}V_3Ge_1P_{0.1}O_{45.8}$ | 303 | 98.9 | 92.9 | 1.6 | 93.9 |
| 5 | $Mo_{12}V_3Ge_1In_{0.2}O_{45.8}$ | 299 | 99.5 | 94.1 | 1.2 | 94.6 |
| 6 | $Mo_{12}V_3Ge_1Bi_{0.2}O_{45.8}$ | 303 | 90.6 | 85.8 | 0.7 | 95.2 |
| 7 | $Mo_{12}V_3Ge_1R.E._{0.5}O_{46.3}$ | 300 | 89.3 | 85.4 | 0.7 | 96.0 |
| 8 | $Mo_{12}V_3Ge_1Tl_{0.2}Cu_{0.1}O_{45.9}$ | 306 | 99.1 | 94.0 | 1.3 | 94.8 |

(1) 20% active component on 3/16" Alundum spheres.

We claim:

1. The process for the production of acrylic acid or methacrylic acid from acrolein and methacrolein, respectively, with molecular oxygen optionally in the presence of steam at a temperature of about 200° to about 500° C employing a catalyst having the empirical formula:

$$Mo_aV_bGe_cX_dY_eO_f$$

wherein X can be one or more of the elements selected from the group consisting of iron, nickel, thallium, phosphorus, indium, bismuth, and the rare earths; and Y can be one or more of the elements of the group consisting of copper, tin, chromium, manganese, magnesium, aluminum, titanium, arsenic, niobium, tantalum, potassium, rubidium, cesium, tungsten, uranium, cobalt, silver, gallium, antimony, and zinc; and wherein the number of atoms of each element present is represented by $a$ through $f$, wherein $a$ is a number from 6 to 18;
$b$ is a number from 0.1 to 10;
$c$ is a number from 0.1 to 6;
$d$ is a number from 0.01 to 5;
$e$ is a number from 0 to 5;
$f$ is a number that satisfies the valence requirements of the other elements present.

2. The process in claim 1 wherein acrylic acid is prepared from acrolein.

3. The process of claim 1 wherein in the catalyst formula $a = 9$ to 15; $b = 0.5$ to 5; $c = 0.5$ to 3; $d = 0.05$ to 1; $e = 0.0$ to 1; and $f$ is a number that satisfies the valence requirements of the other elements present.

4. The process in claim 1 wherein in the empirical formula X is iron.

5. The process in claim 1 wherein in the empirical formula X is thallium.

6. The process in claim 1 wherein in the empirical formula X is phosphorus.

7. The process in claim 1 wherein in the empirical formula X is bismuth.

8. The process in claim 1 wherein in the empirical formula X is indium.

* * * * *